US006077250A

United States Patent [19]

Snow et al.

[11] Patent Number: 6,077,250

[45] Date of Patent: Jun. 20, 2000

[54] APPARATUS AND METHOD FOR PERCUTANEOUSLY PLACING GASTROSTOMY TUBES

[75] Inventors: Todd Snow, Westboro; Michael Chu, Brookline, both of Mass.

[73] Assignee: Boston Scientific Corporation, Natick, Mass.

[21] Appl. No.: 08/942,577

[22] Filed: Oct. 1, 1997

[51] Int. Cl.[7] .......... A61M 5/32

[52] U.S. Cl. .......... 604/174; 604/178; 604/910; 604/523; 128/DIG. 26

[58] Field of Search .......... 604/174, 93, 523, 604/910, 170, 104, 106, 264, 164, 178; 128/DIG. 26

[56] References Cited

U.S. PATENT DOCUMENTS

| | | | |
|---|---|---|---|
| Re. 31,855 | 3/1985 | Osborne . | |
| B1 Re. 31,855 | 8/1986 | Osborne . | |
| 3,910,272 | 10/1975 | Forberg . | |
| 4,581,025 | 4/1986 | Timmermans . | |
| 4,732,152 | 3/1988 | Wallsten et al. . | |
| 4,776,846 | 10/1988 | Wells . | |
| 4,798,592 | 1/1989 | Parks . | |
| 4,861,334 | 8/1989 | Nawaz . | |
| 4,865,593 | 9/1989 | Ogawa et al. . | |
| 4,874,374 | 10/1989 | Kousai et al. . | |
| 4,883,468 | 11/1989 | Kousai et al. . | |
| 5,007,900 | 4/1991 | Picha et al. . | |
| 5,074,846 | 12/1991 | Clegg et al. | 604/164 |
| 5,080,650 | 1/1992 | Hirsch et al. . | |
| 5,084,014 | 1/1992 | Picha et al. . | |
| 5,098,378 | 3/1992 | Pointek et al. . | |
| 5,104,388 | 4/1992 | Quackenbush . | |
| 5,158,545 | 10/1992 | Trudell et al. . | |
| 5,180,372 | 1/1993 | Vegoe et al. . | |
| 5,195,978 | 3/1993 | Schiffer . | |
| 5,209,741 | 5/1993 | Spaeth . | |
| 5,234,454 | 8/1993 | Bangz | 606/191 |
| 5,248,302 | 9/1993 | Patrick et al. . | |
| 5,279,564 | 1/1994 | Taylor . | |
| 5,318,542 | 6/1994 | Hirsch et al. . | |
| 5,318,543 | 6/1994 | Ross et al. | 604/164 |
| 5,356,391 | 10/1994 | Stewart . | |
| 5,391,159 | 2/1995 | Hirsch et al. . | |
| 5,397,332 | 3/1995 | Kammerer et al. . | |
| 5,405,378 | 4/1995 | Strecker . | |
| 5,429,598 | 7/1995 | Waxman et al. . | |
| 5,454,790 | 10/1995 | Durbrul | 604/104 |
| 5,531,699 | 7/1996 | Tomba et al. | 604/164 |
| 5,536,255 | 7/1996 | Moss | 604/191 |
| 5,555,898 | 9/1996 | Suzuki et al. . | |
| 5,556,411 | 9/1996 | Taoda et al. . | |
| 5,928,208 | 7/1999 | Chu et al. | 604/280 |
| 5,941,855 | 8/1999 | Dicha et al. | 604/174 |

FOREIGN PATENT DOCUMENTS

| | | |
|---|---|---|
| WO 94/27655 | 12/1994 | WIPO . |
| WO 94/27656 | 12/1994 | WIPO . |
| WO 95/20936 | 8/1995 | WIPO . |

OTHER PUBLICATIONS

Literature on "Zeus Heat Shrink Tubing of 'Teflon®'", Zeus Industrial Products, Inc., Catalog pp. 23–24.

Literature on "The Zeus Family of Fluoropolymers", Zeus Industrial Products, Inc., Catalog p. 4.

*Primary Examiner*—Corrine McDermott
*Assistant Examiner*—Cris L. Rodriguez
*Attorney, Agent, or Firm*—Kenyon & Kenyon

[57] ABSTRACT

An apparatus and method for percutaneously placing gastrostomy tubes. The method enables percutaneous placement through an existing penetration, as well as placement where no penetration exists. The apparatus comprises a gastrostomy tube having an internal bolster which can be manipulated such that it has a reduced lateral extent; an axially-extending hollow sleeve which can surround the bolster to hold it in a position of reduced lateral extent; and a rip-cord capable of tearing the sheath. In a preferred embodiment, the internal bolster is folded to have a smaller diameter, the sleeve is placed over the bolster and shrunk down to a smaller diameter. The rip-cord runs distally along the outside of the tube, between the sleeve and the internal bolster, wraps over the distal end of the sleeve and runs proximally along the length of the tube. The replacement tube can then be pushed through a stoma. Once in place, the rip cord is pulled to tear away the sleeve, thereby allowing the bolster to revert to its original lateral extent.

21 Claims, 13 Drawing Sheets

APPARATUS AND METHOD FOR PERCUTANEOUSLY PLACING GASTROSTOMY TUBES

FIELD OF THE INVENTION

The present invention relates generally to an apparatus and method for the percutaneous placement of gastro-intestinal devices. More specifically, the present invention relates to an apparatus and method for percutaneously placing one type of gastro-intestinal device, gastrostomy tubes having internal bolsters, by using a hollow sleeve to hold the bolster in a position such that it has a reduced lateral extent during placement, and a rip cord to release the sleeve from around the bolster.

BACKGROUND OF THE INVENTION

Medical practitioners currently use Percutaneous Endoscopic Gastrostomy (PEG) and Percutaneous Endoscopic Jejunostomy (PEJ) techniques to place catheters or tubes within the gastro-intestinal tract. Three main PEG techniques are used to place gastro-intestinal tubes: Sacks-Vine, Ponsky, and Russell. These techniques are well-known in the art.

Gastrostomy tubes, which are a type of gastro-intestinal tubes, often have an anchoring device, or internal bolster, on their distal ends. These bolsters are formed with a lateral extent which is wider than the penetration diameter to prevent premature removal of the tube from the penetration. The bolsters often have a dome, mushroom, or Malecot structure.

Due to the lateral extent with which the internal bolsters are formed, percutaneous placement of tubes having such bolsters through a penetration is difficult, and current techniques do not adequately provide for placement of such tubes. When placing a gastrostomy tube with internal bolster at its distal using either Sacks-Vine or Ponsky technique, for example, the tube and bolster are dragged through the esophagus and into the stomach. When performing percutaneous placement according to the Russell technique, practitioners typically use catheters with a balloon on the distal end which can be inflated once the tube is placed within the stomach, instead of using a tube having a bolster with lateral extent as described above.

Typically, the initial penetration is maintained such that a stoma, or fistulous tract, is allowed to form, which connects the stomach wall to the external abdominal wall. In the prior art, the initially-placed gastrostomy tubes are replaced using the same techniques used as to place the initial tube; i.e. according to either the Sacks-Vine, Ponsky, or Russell technique. Alternatively, they are placed by insertion through the stoma.

Various devices have been used for inserting a gastro-intestinal tube having an internal bolster through a stoma. Use of these devices typically involves obturating or realigning the internal bolster, or axially elongating the internal bolster prior to insertion. See e.g., U.S. Pat. Nos. 5,248,302, 5,007,900, and 5,454,790.

Several deficiencies exist in the prior art techniques. For example, Russell technique is a complicated placement method which is not conducive to placing gastrostomy tubes having internal bolsters. In addition, those techniques which use obturation for placing tubes by insertion through a stoma often require specialized bolsters capable of engaging an obturator rod, and access tubes equipped with such specialized bolsters are typically expensive. See e.g, U.S. Pat. No. 5,248,302. Furthermore, prior art techniques which involve axial elongation and radial compression of the access tube require a grade of access tube which can sustain such axial tension and radial compression. See e.g. U.S. Pat. No. 5,454,790. Those techniques may also require a sheath capable of compressing the tube to a diameter smaller than the diameter when under axial tension or radial compression. Further still, techniques used with access tubes having T-bar bolsters in which the T-bar bolster is aligned with the tube shaft, such as that described in U.S. Pat. No. 5,007,900, often do not sufficiently reduce the lateral extent of the tube's distal end to a size that can be easily inserted into the stoma.

SUMMARY OF THE INVENTION

The present invention is directed to an apparatus and method which facilitate percutaneous placement of a gastro-intestinal device, such as a gastrostomy tube, either through an existing penetration or by insertion where no prior penetration exists. The apparatus comprises a gastrostomy tube having a deformable internal bolster, a hollow sleeve, and a rip-cord. The hollow sleeve is a substantially tubular structure with a lubricious outer surface. The sleeve fits around the internal bolster and holds the bolster in a position such that the lateral extent of the bolster is reduced. The sleeve can be made of material that allows the sleeve to be changed to a substantially tubular form having a reduced diameter. For example, the sleeve can shrink or contract to a reduced diameter. Alternatively, the hollow sleeve can be made such that a bolster can be compressed and slid or otherwise placed within the hollow sleeve. The rip-cord is a filament, such as wire, string or fibrous thread, capable of tearing through the hollow sleeve, thereby releasing the bolster and allowing the bolster to regain its original lateral extent.

One embodiment of the present invention enables the percutaneous placement of a gastrostomy tube through an existing penetration by pushing an assembled device through the penetration, with this embodiment comprising a gastrostomy tube, a rip-cord, and a hollow sleeve. In this embodiment, the bolster is first manipulated such that its lateral extent is reduced. This manipulation can be performed by re-positioning, folding, compressing, or stretching the bolster, or a combination thereof. The lateral extent of the bolster can be reduced to a size approximately equal to or less than the tube diameter, thereby facilitating placement through the existing penetration. The hollow sleeve is placed so as to surround the rip-cord and the manipulated internal bolster, and may additionally extend to cover a portion of the tube shaft. The sleeve is preferably made of a heat-shrinkable fluoropolymer tubing, such as tetrafluorethylene (TFE) tubing, which, when heated, shrinks to fit snugly around the bolster, holding it in its manipulated position of reduced lateral extent. The rip-cord preferably runs between the gastrostomy tube shaft and the hollow sleeve, wraps over the top of the sleeve, extending proximally along the tube shaft.

The assembled apparatus can then be inserted into the existing penetration by holding the tube shaft and pushing the assembly through the penetration. In addition, the hollow sleeve can be placed such that it extends to cover a portion of the tube shaft, thereby providing additional support to the shaft and decreasing shaft buckling during insertion.

Another embodiment of an apparatus according the present invention includes an extension rod and an internal bolster with one or more pockets capable of receiving the tip of the extension rod. The rod, which is used to push the tube through the existing penetration, can be inserted through the central lumen of the gastrostomy tube to reach the bolster pocket. Alternatively, the rod can be run inside of the hollow sleeve into the pocket, or along the outside of the sleeve and into the bolster pocket.

The shaft of the gastrostomy tube may have a slit through which the extension rod can pass. The rod can be inserted into the central lumen of the tube, run so as to exit the lumen through the slit and rest within the pocket of the bolster. The slit closes upon removal of the rod, such that no materials (e.g. food or medication) can exit the tube through the slit during use of the tube.

Yet another embodiment of the apparatus of the present invention enables percutaneous placement where no penetration exists. This embodiment includes a trocar which can be used to pierce the body tissue and form a penetration. The trocar has a tapered distal end and, in addition, may have a wedge or ridge, located on the trocar shaft proximal to the tip, which tapers proximally.

The apparatus of this embodiment is assembled such that the sleeve surrounds the tube, bolster, and trocar. The tapered distal tip, however, extends distal to the distal end of the sleeve. The trocar can be inserted through the central lumen of the tube or, alternatively, the trocar can be run along the outside of the tube, inside of the sleeve. The trocar wedge engages the internal bolster or another portion of the assembly, preventing the hollow sleeve, internal bolster, and gastrostomy tube from being pushed proximally, with respect to the trocar, during insertion. The wedge essentially holds the assembly together as a unit during insertion.

Still another embodiment of the apparatus of the present invention includes a cannula which can be used to percutaneously place the gastrostomy tube over a guidewire. In addition, the internal bolster may have a bore through its entire width, such that a cannula or trocar can run therethrough.

The apparatus of the present invention overcomes the deficiencies of prior art devices in that it eliminates the need to insert the initial placement tube according to traditional PEG methods such as Sacks-Vine, Ponsky, or Russell.

In addition, the present invention can be used with a wide range of internal bolsters. Prior art replacement PEG devices utilize specialized bolsters adapted for a particular placement technique. The present invention operates with all internal bolsters which can be folded, compressed, stretched or otherwise reduced in effective diameter. Most of the bolsters currently used are made of biocompatible polymers such as silicone elastomer, silicone copolymer, or polyurethane, and can be folded to a reduced diameter. Thus bolsters with mushroom, dome, malecot, or other configurations can be used.

Using the percutaneous replacement method of the present invention, the gastro-intestinal tube, hollow sleeve, and rip-cord are assembled such that the hollow sleeve is placed over the internal bolster, holding it in a reduced diameter form; the rip-cord extends distally along the longitudinal axis of the tube, positioned between the hollow sleeve and the gastro-intestinal tube, wraps over the distal end of the sleeve, and then extends proximally along the longitudinal axis of the tube, on the outside of the sleeve. Next, the distal end of the tube is pushed through the stoma until the tube is fully inserted. The rip-cord is then pulled, tearing the hollow sleeve from the distal towards the proximal end, and thereby releasing the bolster. The sleeve and rip-cord are then pulled from the stoma, leaving the gastro-intestinal tube in place.

To facilitate placement, the gastro-intestinal tube may have an insertion handle on its proximal end.

To facilitate sleeve removal, the hollow sleeve may be longitudinally scored to aid removal. Further, two longitudinal slits may be made 180° apart at the proximal sleeve end. These slits form tabs which may be used to pull the sleeve from the stoma. Still further, a tab may be attached to the end of the rip-cord to facilitate pulling the cord.

In addition, the sleeve can be made such that the rip-cord is integrally formed within the sleeve. This can be done using molding techniques known in the art. The rip-cord would be run along the inner length of the sleeve such that the rip-cord would tear through the sleeve when pulled.

An alternate replacement method of the present invention applies to the embodiment, described above, in which the internal bolster contains a pocket capable of receiving an extension rod. The method of inserting this embodiment includes essentially the same steps as those in the method described above. In this alternate method, however, the apparatus is assembled such that the pocket is left exposed. The rod is inserted into the pocket and used to push the assembly through the penetration. The rod is then removed from the penetration along with the sleeve and rip-cord.

BRIEF DESCRIPTION OF THE DRAWINGS

The invention will be more readily understood through the following detailed description, with reference to the accompanying drawings, in which.

DETAILED DESCRIPTION OF THE INVENTION

Figures 1A, 1B, 2A, 2B:
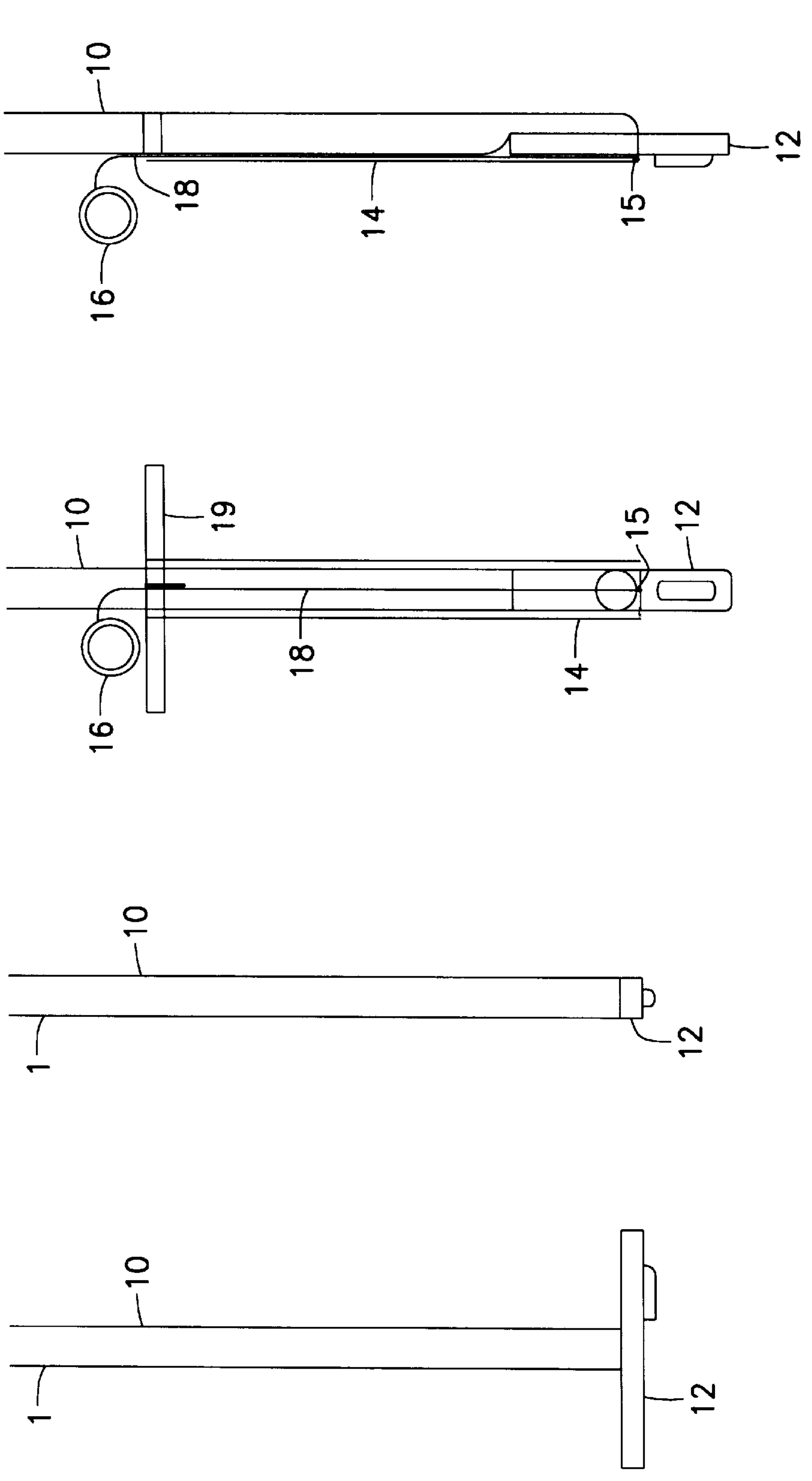
Fig. 1b Prior Art
Fig. 1a Prior Art
FIG. 1*a* is an elevational view of a prior art gastrostomy tube with a deformable internal bolster attached to the distal end.
FIG. 1*b* is a side view of the prior art gastrostomy tube in FIG. 1.
FIG. 2*a* is an elevational view of an embodiment of a gastrostomy tube placement assembly according to the present invention.
FIG. 2*b* is a side view of the gastrostomy tube placement assembly shown in FIG. 2*a*.
Figure 2C:
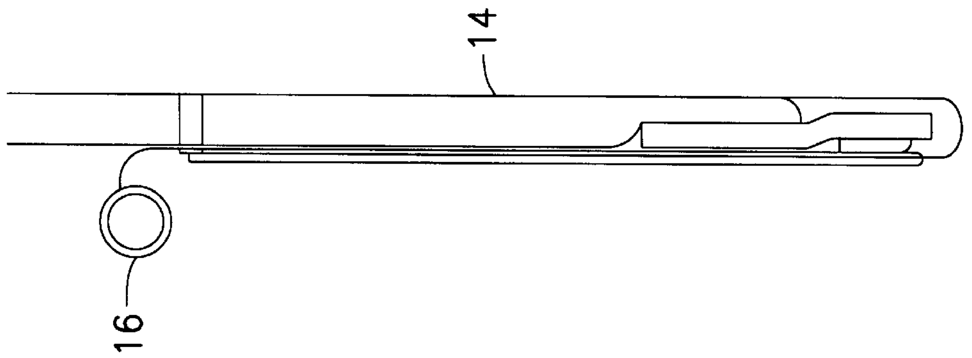
FIG. 2*c* is an elevational view of an embodiment of a gastrostomy tube placement assembly according to the present invention with the hollow sleeve extending distal to the internal bolster.

FIGS. 1*a* and 1*b* show a prior art gastrostomy tube 1 with a tube shaft 10 and attached internal bolster 12. The tube 1 has a distal end for insertion into the patient, and a proximal end for extending out of the patient through a stoma or other penetration, with the bolster 12 located at the distal end.

Figure 10:
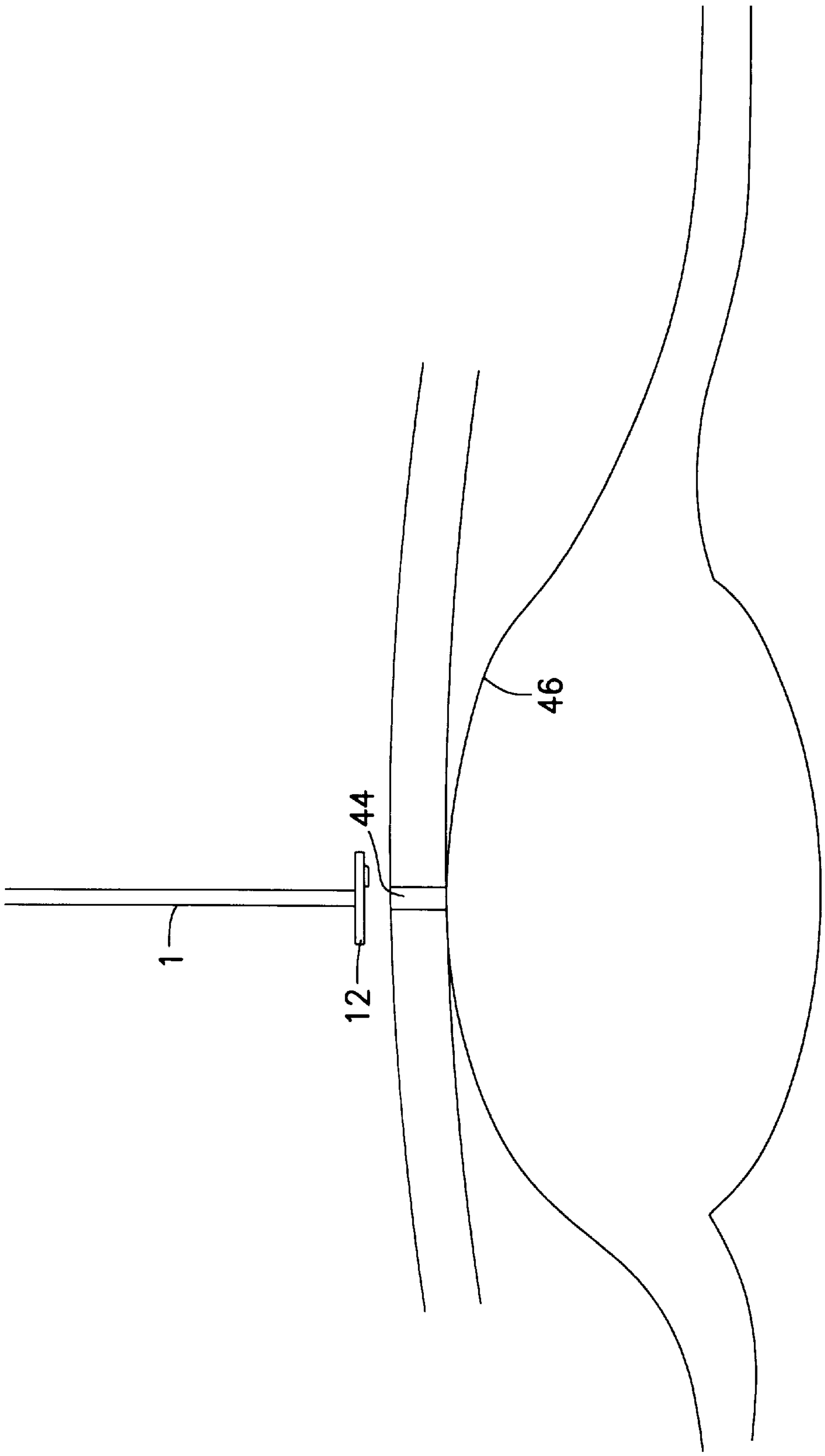
Fig. 10 Prior Art
FIGS. 10 shows a cross sectional view of the abdominal wall and stomach, and an elevational view of a prior art gastrostomy tube in relation to a stoma.

FIG. 10 generally shows the geometrical relation of a gastrostomy tube with a bolster 12 to a stoma 44, where the bolster has not been re-position or otherwise manipulated. In such an un-altered state, the bolster 12 has a lateral extent which is wider than the diameter of the stoma 44 through which the tube 1 is being placed, so that once inserted the risk that the tube will be removed prematurely through the penetration is reduced. This same lateral extent makes direct tube placement through the stoma 44 difficult. For purposes of insertion, the effective lateral extent of the tube is that of the bolster 12, since, for direct insertion, bolster 12 has to pass through the stoma before the tube shaft 10. The present invention facilitates such direct percutaneous placement by reducing the effective insertion diameter of the tube.

FIGS. 2*a* and 2*b* show an embodiment of the apparatus according to the present invention. As shown in these figures, the internal bolster 12 is manipulated or re-positioned so as to reduce the lateral extent of the bolster 12. Specifically, the bolster 12 is re-positioned such that the bolster 12 is aligned along the axis of the tube 10. Alternatively, the bolster 12 can be folded, compressed, or stretched such that the lateral extent of the bolster 12 is reduced.

Figure 3:
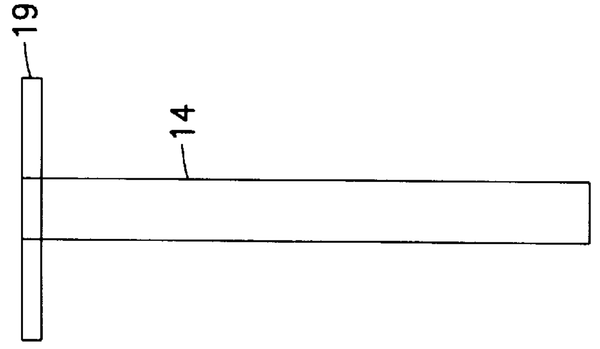
FIG. 3 is an elevational view of a hollow sleeve of the present invention with proximal flanges.

A hollow sleeve 14, shown in FIG. 3, is inserted over the bolster 12 and shrunken, contracted, or otherwise reduced in diameter so as to hold the bolster 12 in the position of reduced lateral extent. The hollow sleeve 14 can also be molded or wrapped around the bolster 12 and tube 1 so as to reduce the lateral extent of the bolster 12. Alternatively, the bolster can be pushed or pulled into the sleeve 14, thereby reducing the lateral of the bolster.

The sleeve 14 is made of a material which can shrink or contract to hold the bolster 12 in the re-positioned state. The sleeve 14 is preferably made of a heat-shrinkable fluoropolymer, such as tetrafluoroethylene (TFE). Material suitable for use as the hollow sleeve is made by Zeus Industrial Products, Inc. and marketed under the name Zeus Heat Shrink Tubing. When heated, the hollow sleeve 14 shrinks to a reduced diameter, holding the bolster 12 in the manipulated state. The hollow TFE sleeve 14 may also have proximal tabs 19 which can be used to facilitate removal of the sleeve 14 from the penetration.

Also in this embodiment is a rip-cord 18 which runs distally along the longitudinal axis of the tube shaft 10 and between the hollow sleeve 14 and manipulated bolster 12, then wraps over the distal end of the sleeve 14 and runs proximally along the outer surface of the sleeve 14 generally parallel to the longitudinal axis of the tube shaft 10.

The rip-cord 18 is preferably made of suture wire, but can also be made of a filament, which is any wire-like material capable of ripping the sleeve 14, such as dental floss, suture wire or other suitable fibrous thread.

The sleeve 14 is preferably made of a material which can be ripped cleanly by the rip-cord 18. Tetrafluoroethylene (TFE) allows a linear tear path and will not bind the rip-cord 18 as it tears through the sleeve 14. A nick 15 may made in the sleeve 14 at the distal end which facilitates tearing the sleeve by providing a start for the tear. Prior to the being pulled, the rip-cord 18 sits in the nick 15.

The sleeve 14 can be manufactured such that the rip-cord 18 is integrally formed with the sleeve 12. The rip-cord 18 would run along the inner length of the sleeve 14 such that, when pulled, it would axially tear through the sleeve 14.

Figure 4:
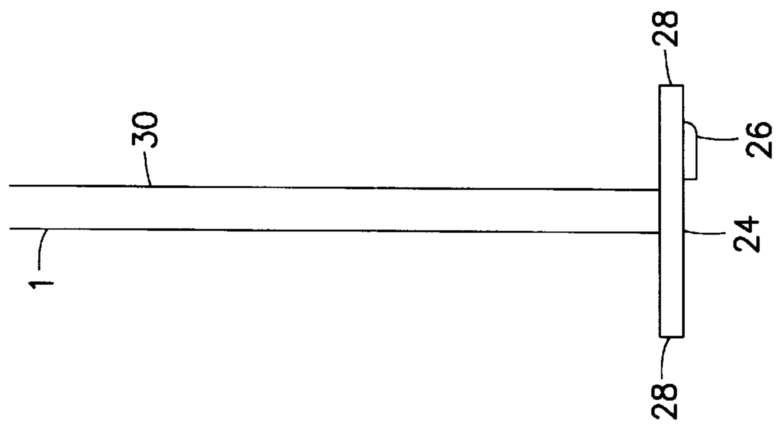
Fig. 4 Prior Art
FIG. 4 is an elevational view of a prior art gastrostomy tube which has an internal bolster having a pocket.

FIG. 4 shows a prior art gastrostomy tube that is used in another embodiment of the invention. In this embodiment, the internal bolster 24 has one or more pockets 26 capable of receiving an extension rod 21, shown in FIGS. 6*a* and 6*b*, which is used to push the replacement tube through the penetration 44. The bolster also has a hole 25, which is aligned with the central lumen of the tube shaft 30. The gastrostomy tube, shown in FIG. 4 has a T-bar internal bolster 24 at its distal end with flanges 28, and a pocket 26 on one of the T-bar flanges 28. As an alternative to the flange pocket, the junction of the bolster itself with the replacement tube can itself serve as a pocket for receiving an extension rod.

Figure 6B:
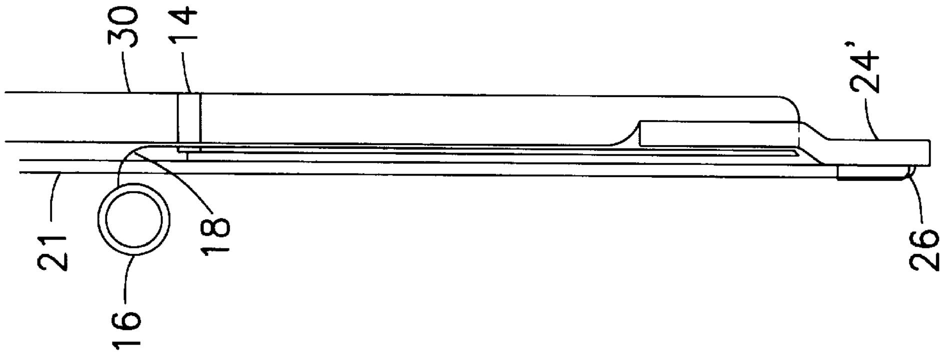
FIG. 6*b* is an elevational view of another embodiment of a gastrostomy tube placement assembly of the present invention with an extension rod external to the hollow sleeve.
Figure 6A:
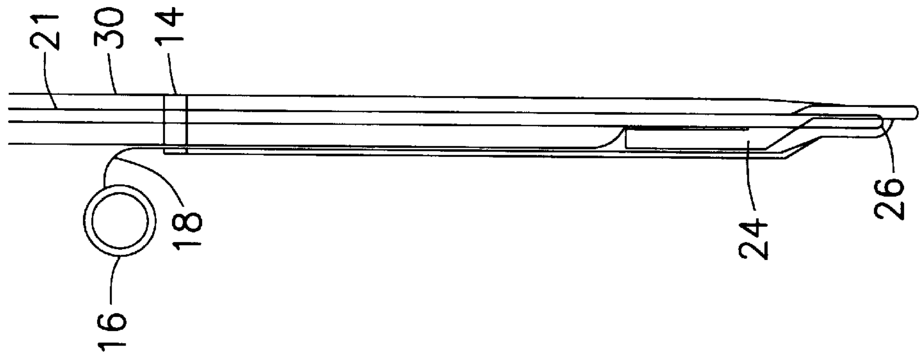
FIG. 6*a* is an elevational view of another embodiment of a gastrostomy tube placement assembly of the present invention with the hollow sleeve surrounding an extension rod.
Figure 5:
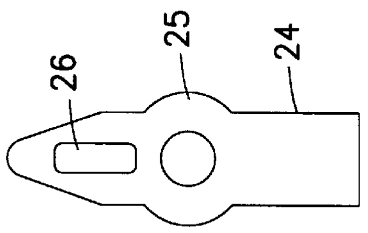
FIG. 5 is a distal end view of the prior art gastrostomy tube, shown in FIG. 4.

In accordance with the present invention, the T-bar internal bolster 24 is re-positioned so as to be aligned along the longitudinal axis of the tube shaft 30, as shown in FIGS. 6*a* and 6*b*. The hollow sleeve 14 is then inserted over the T-bar 24 and shrunken or contracted so as to reduce the effective lateral extent for insertion to approximately that of the tube shaft 30. The hollow sleeve 14 can be further shrunken or contracted such that the effective lateral extent for insertion is narrower than the diameter of the tube shaft 30.

Where a T-bar flange 28 having a bolster pocket 26 as shown in FIG. 4 is employed, and the extension rod 21 is inserted after the hollow sleeve 14 is placed and shrunken or contracted, the sleeve 14 should be placed so as to leave the bolster pocket 26 sufficiently exposed to allow reception of the extension rod 21. This can be accomplished either by longitudinally slitting or cutting that portion of the sleeve 14 that will cover the pocket 26, or by positioning the sleeve 14 so that it does not cover the pocket 26. The extension rod 21 can be inserted such that it is surrounded by the sleeve 14, as shown in FIG. 6*a*, or such that it is external to the sleeve 14, as shown in FIG. 6*b*.

Figure 8C:
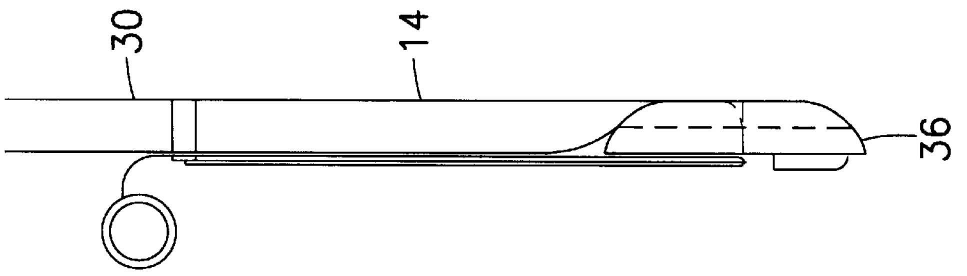
FIG. 8*c* is an elevational view of a gastrostomy tube placement assembly according to the present invention where the gastrostomy tube has an internal bolster with a disk configuration which is wrapped around the tube shaft.
Figure 8B:
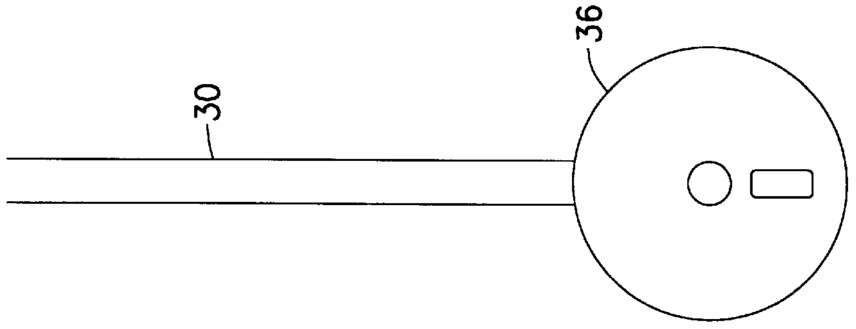
FIG. 8*b* is an elevational view of a gastrostomy tube having an internal bolster with a disk configuration with the bolster in a re-positioned state in which is deflected 90°.
Figure 8A:
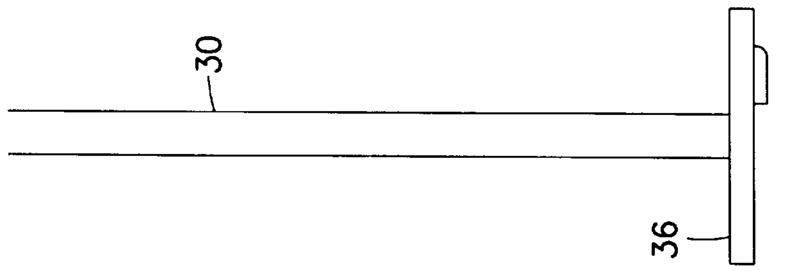
FIG. 8*a* is an elevational view of a gastrostomy tube having an internal bolster with a disk configuration.

It will be appreciated that the shape of the internal bolster 14 is not critical. A bolster of any shape can be used in conjunction with this invention, as long as the bolster can be manipulated or re-positioned to reduce the effective lateral extent of the tube for insertion. FIGS. 8*a*–8*c* show a bolster 36 with a disk configuration. FIG. 8*b* shows the bolster turned 90° with respect to the tube. This is generally accomplished by bending the tube at its junction with the bolster. This is especially practical where the tube is made of a relatively soft material. Where a harder material is employed, the bolster itself may be deformed in the area of its junction with the tube in order to effect its 90° reorientation. FIG. 8*c* shows the bolster 36 in a re-positioned state, such that the bolster is wrapped or folded around the tube shaft 30 The hollow sleeve 14 is then inserted over or formed around the re-positioned or folded bolster 36, shown in FIG. 8*b*, holding it in the re-positioned state.

Figure 9B:
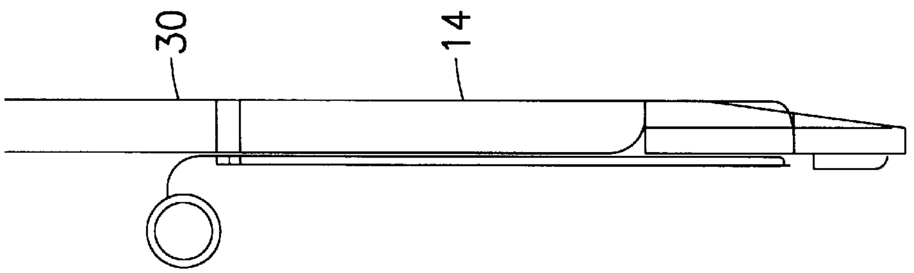
FIG. 9*b* is an elevational view of a gastrostomy tube placement assembly according to the present invention where the gastrostomy tube has an internal bolster with a triangular configuration and where the distal end of the tube is bent and compressed, the bolster is wrapped around the tube shaft, and the hollow sleeve holds the bolster in a substantially cylindrical configuration.
Figure 9A:
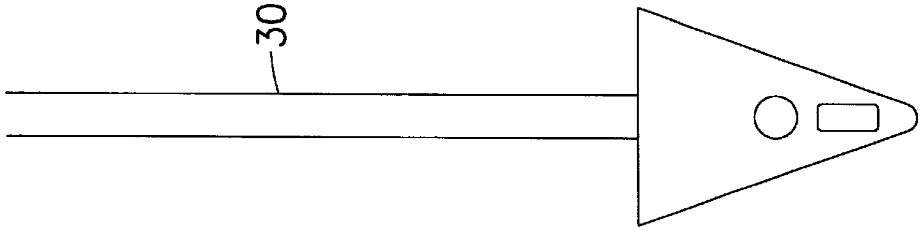
FIG. 9*a* is an elevational view of a gastrostomy tube having an internal bolster having a triangular configuration in which the bolster is in a re-positioned state.

FIGS. 9*a* and 9*b* show a bolster with a triangular configuration.

It will also be appreciated that a number of materials can be used for the tube shaft 30 in accordance with the present invention. When stiffer materials are used to make the tube shaft 30, it can essentially serve as its own insertion rod, allowing the practitioner to hold the tube shaft while pushing the assembly through the penetration. In addition, an insertion handle can be placed or attached to the proximal end of the tube shaft 30 to aid in insertion. When less stiff materials are used for the tube shaft 30, the hollow sleeve 14 can be inserted over the bolster 26 such that the sleeve 14 also extends down the tube shaft 30 for a length, as shown in FIG. 6*a* and 6*b*. The sleeve 14 supports the tube shaft 30, allowing direct insertion through the penetration. In this configuration, insertion can be performed by holding the tube shaft 30 and pushing the tube through the stoma 44.

Figure 7:
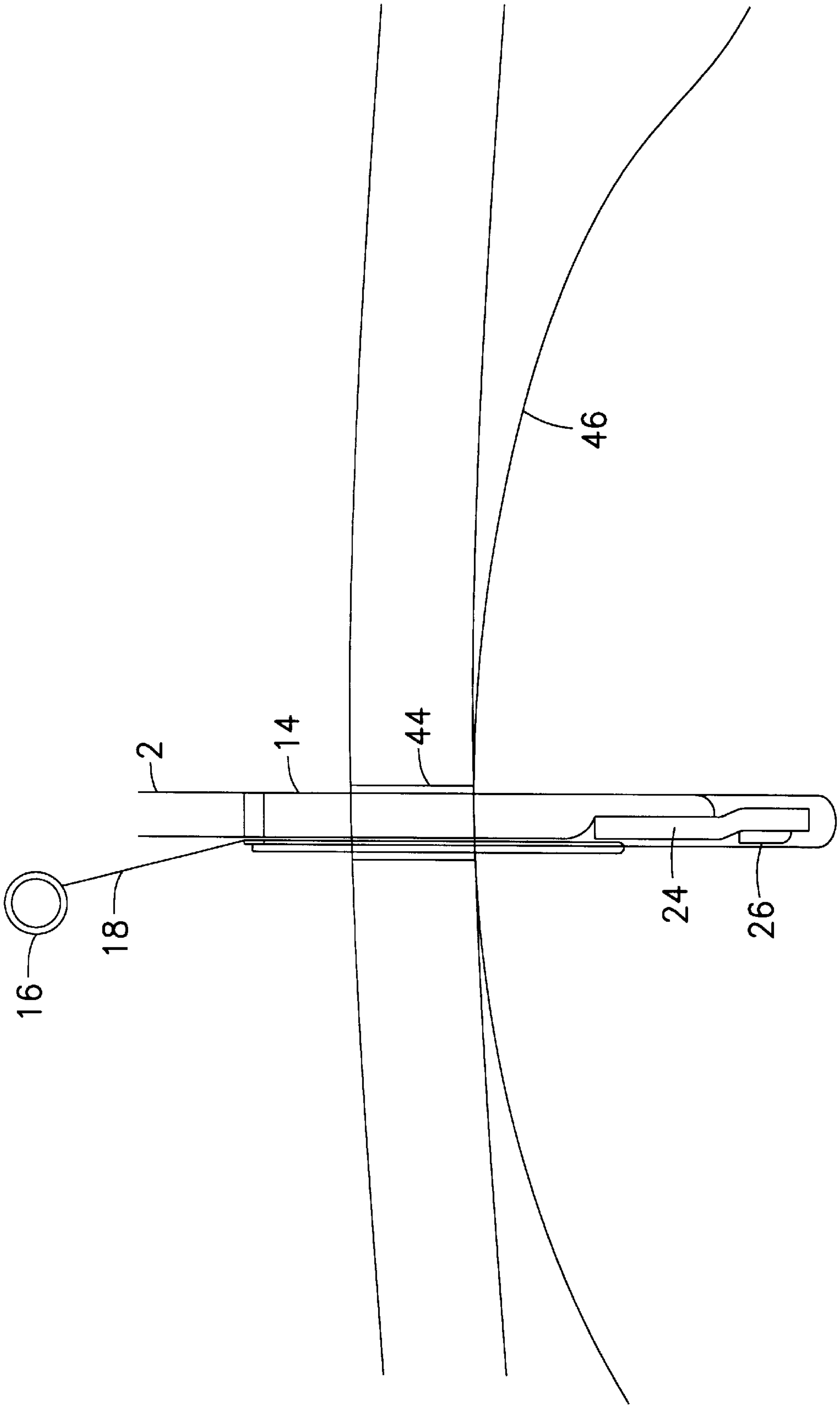
FIG. 7 is a cross sectional view of an abdomen with a gastrostomy tube placement assembly of the present invention placed within a penetration, prior to release of the bolster.

FIG. 7 shows the gastrostomy tube placement assembly after it has been pushed through the stoma 44, prior to removal of sleeve 14. To facilitate sleeve 14 removal, the hollow sleeve 14 may be longitudinally scored. Further, two longitudinal slits may be made 180° apart at the proximal sleeve end to form tabs which can be used to pull the sleeve 14 from the stoma 44. Gripping tabs 19 may otherwise be provided at the proximal end of the sleeve 14 to aid in sleeve removal, as shown in FIG. 3. Still further, a means for pulling the rip cord, such as a tab or pull ring 16, may be attached to the end of the rip-cord 18 to facilitate pulling the cord 18.

Figure 14A:
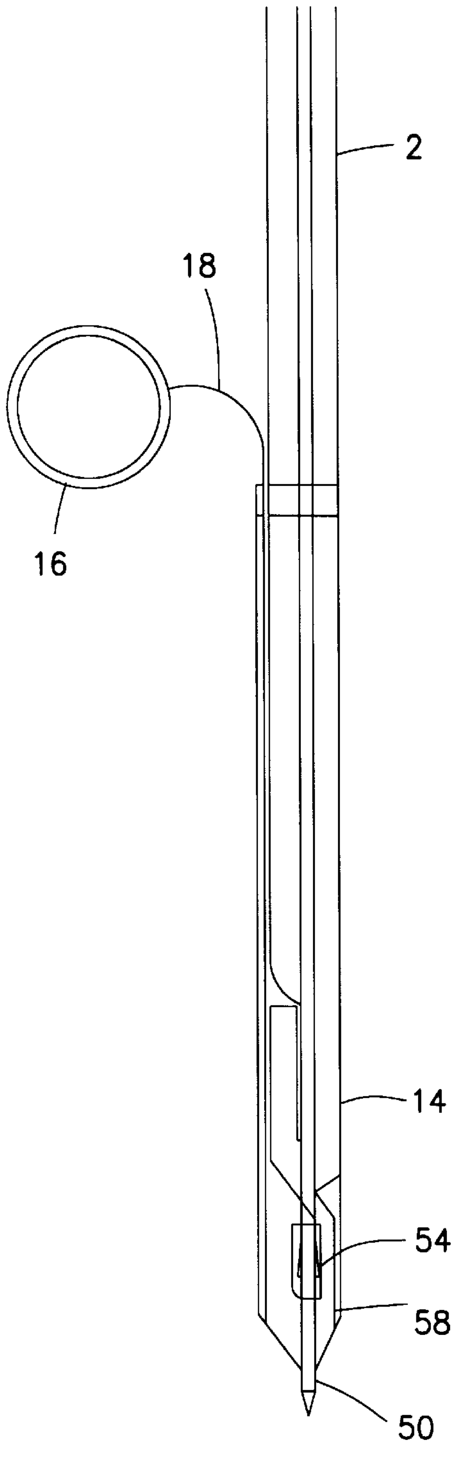
FIG. 14*a* is an elevational view of an embodiment of the apparatus according to the present invention in which the gastrostomy tube placement assembly includes a trocar.
Figure 14B:
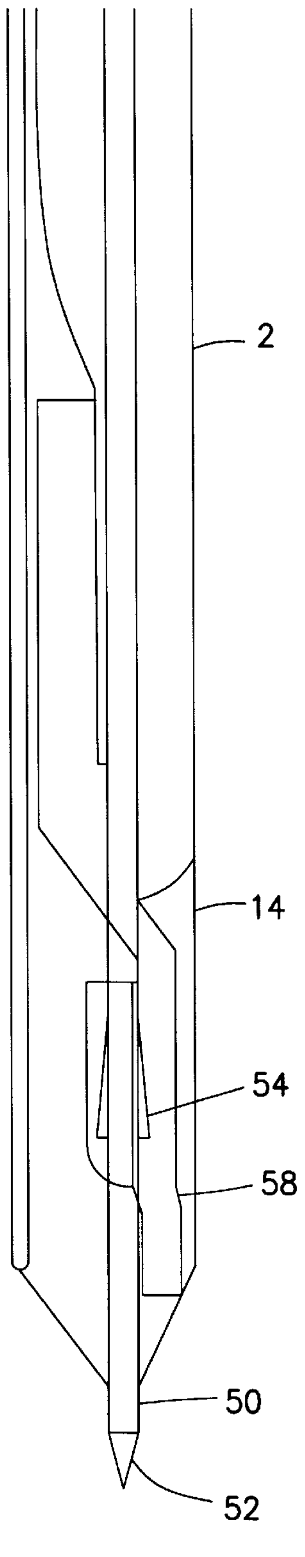
FIG. 14*b* is an enlarged view of the embodiment shown in FIG. 14*a*.

FIG. 14*a* shows yet another embodiment of a gastrostomy tube placement assembly according the present invention which can be used to insert a gastrostomy tube where there is no existing penetration. FIG. 14*b* shows an enlarged view of the embodiment shown in FIG. 14*a*. This embodiment includes a trocar 50 which is used to pierce and penetrate the abdominal tissue and target organ wall. The device (or assembly) 2 is assembled such that the hollow sleeve 14 is placed around the trocar 50, and the distal tip 52 of the trocar extends past the distal end of the hollow sleeve 14, as shown in FIGS. 14*a* and 14*b*.

The trocar 50 in FIG. 14*a* has a distal tip 52 which is tapered to facilitate insertion into the body tissue. The trocar can additionally have a tapered wedge 54 which is used to ensure that, during insertion, the sleeve 14 and bolster 12 are not pushed proximally with respect to the trocar 50 by the body tissue. FIG. 14*a* shows such a tapered wedge 54, which is tapered proximally, and located on the trocar shaft proximal to the distal tip. The trocar 50 is inserted through the central lumen of the gastrostomy tube, and through the opening at the distal tube end. The bolster in FIG. 14*b* is a T-bar with a pocket member 55, which has a bore running through it. The bolster is repositioned such that it is turned 90° with respect to the tube, and the trocar is run through the bore of the pocket member 55. The wedge 54 pushes against the inner surface of the bore of the pocket member 55, thereby engaging that inner surface.

Alternatively, the trocar 50 can be positioned so that the tapered wedge 54 engages the hollow sleeve 14, thereby preventing the sleeve 14 and bolster 58 from being pushed proximally with respect to the trocar 50 during insertion. The tapered edge 14 essentially ensures that the assembly is inserted as a unit.

Figure 16:
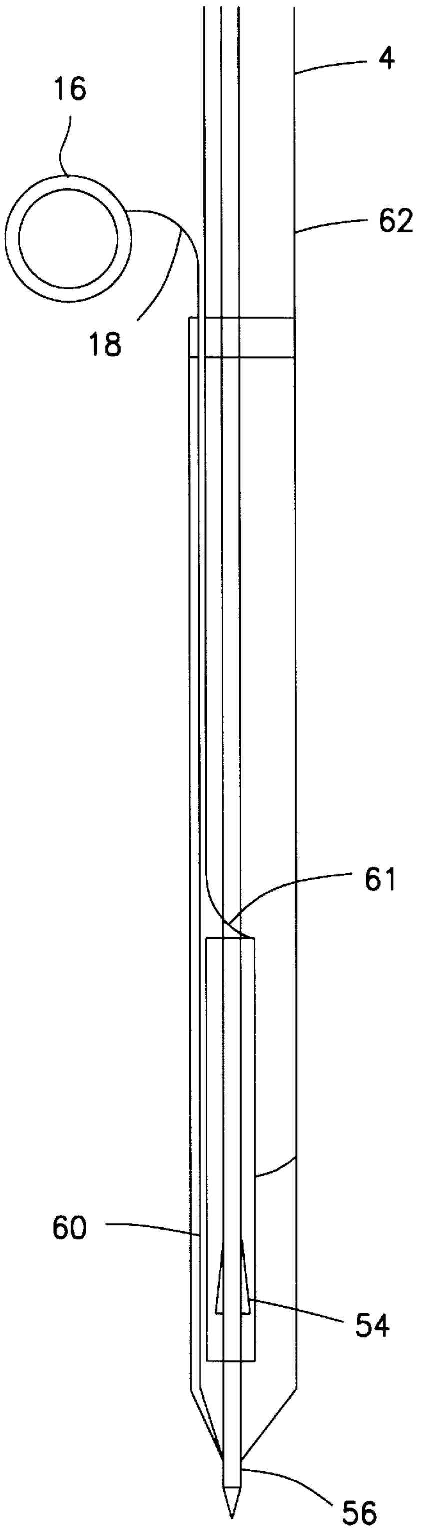
FIG. 16 is an elevational view of an embodiment of the apparatus according to the present invention in which the gastrostomy tube placement assembly includes a trocar, the hollow sleeve extends distal to the internal bolster and has a tapered distal end, the tube shaft has a slit in its lumen, and the bolster has a bore through its width.

FIG. 16 shows a gastrostomy tube placement assembly 4 of the present invention, which, like that shown in FIG. 14*a* and 14*b*, includes a trocar. In the assembly 4 shown in FIG. 16, however, the internal bolster 60 is a T-bar bolster having a bore through its entire width. The trocar 50 is inserted through the central lumen of the gastrostomy tube, and through the opening 61 at the distal tube end. The bolster is repositioned such that it is turned 90° with respect to the tube, and the trocar is run through the bore of bolster 60. In order to effect such a repositioning, the distal end of the tube 62 is bent and compressed. The wedge 54 pushes against the inner surface of the bore of bolster 60 thereby engaging that inner surface.

Figure 17:
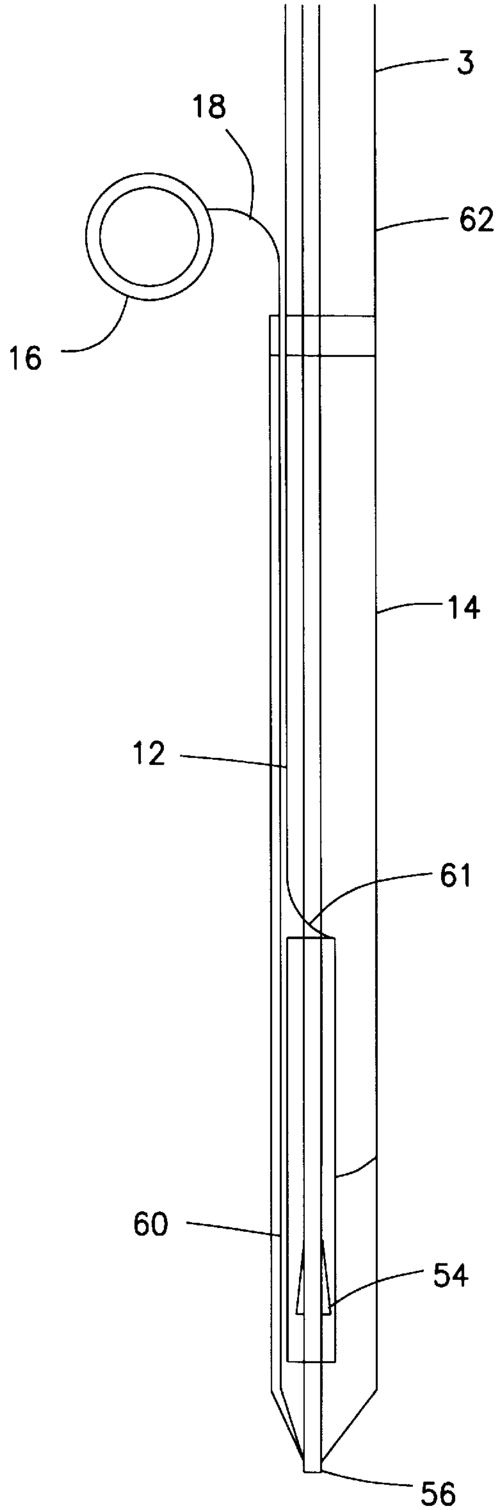
FIG. 17 is an elevational view of an embodiment of the apparatus according to the present invention in which the gastrostomy tube placement assembly includes a cannula, the tube shaft has a slit in its lumen, and the bolster has a bore through its width.

FIG. 17 shows still another embodiment of a gastrostomy tube placement assembly 3 according the present invention which can be used to insert a gastrostomy tube where there is an existing penetration. This embodiment includes a cannula 56 which is used insert the assembly 3 over a guidewire which extends out of the abdominal wall. The internal bolster 60 is a T-bar bolster having a bore through its entire width. The cannula 56 is inserted through the central lumen of the gastrostomy tube, and through the opening 61 at the distal tube end. The bolster is repositioned such that it is turned 90° with respect to the tube, and the trocar is run through the bore of bolster 60. In order to effect such a repositioning, the distal end of the tube 62 is bent and compressed. The wedge 54 pushes against the inner surface of the bore of bolster 60 thereby engaging that inner surface. In addition, the sleeve 14 has a tapered distal end which facilitates insertion.

Figure 11:
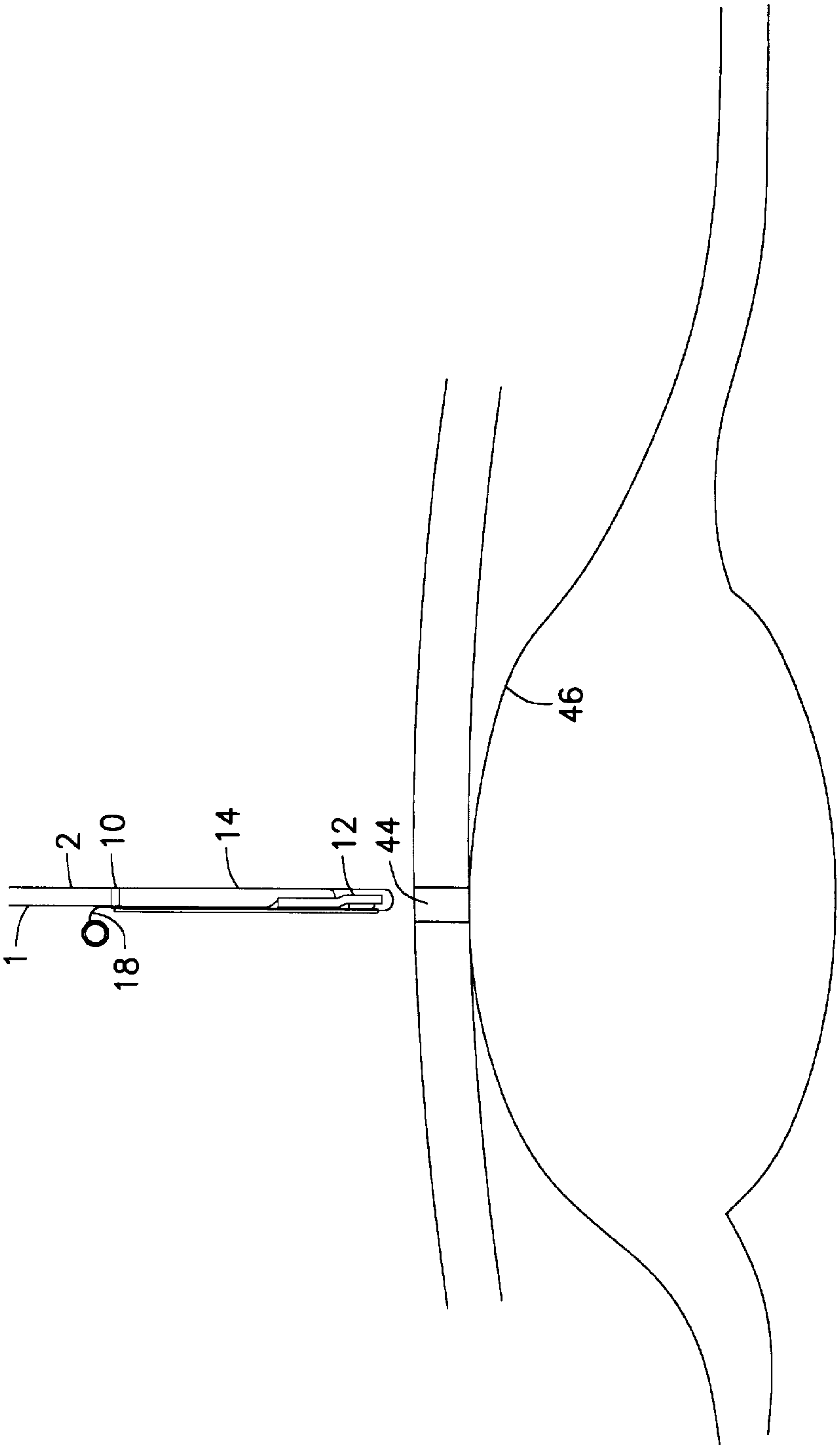
FIGS. 11–13 show a cross-sectional view of the abdominal wall and stomach, and an elevational view of the gastrostomy tube placement assembly in relation to the stoma, illustrating the percutaneous replacement method according to the present invention.

FIGS. 10–13 illustrate the method of replacing a gastrointestinal device, here a gastrostomy tube 1, according the present invention. FIG. 10 shows a gastrostomy tube 1 in relation to a stoma 44. FIG. 11 shows the assembled gastrostomy device in relation to the stoma 44. According to the method of the present invention, a gastrostomy device 2 is assembled such that a hollow sleeve 14 is placed over the internal bolster 12 of a gastrostomy tube 1, holding the bolster 12 in a state in which it has a reduced lateral extent (See FIG. 11). The rip-cord 18 extends distally along the longitudinal axis of the tube shaft 10, running between the hollow sleeve 14 and the internal bolster 12 before wrapping over the distal end of the sleeve and continuing along the outside of the sleeve 14, where it extends proximally generally parallel to the longitudinal axis of the tube shaft 10.

Figure 12:
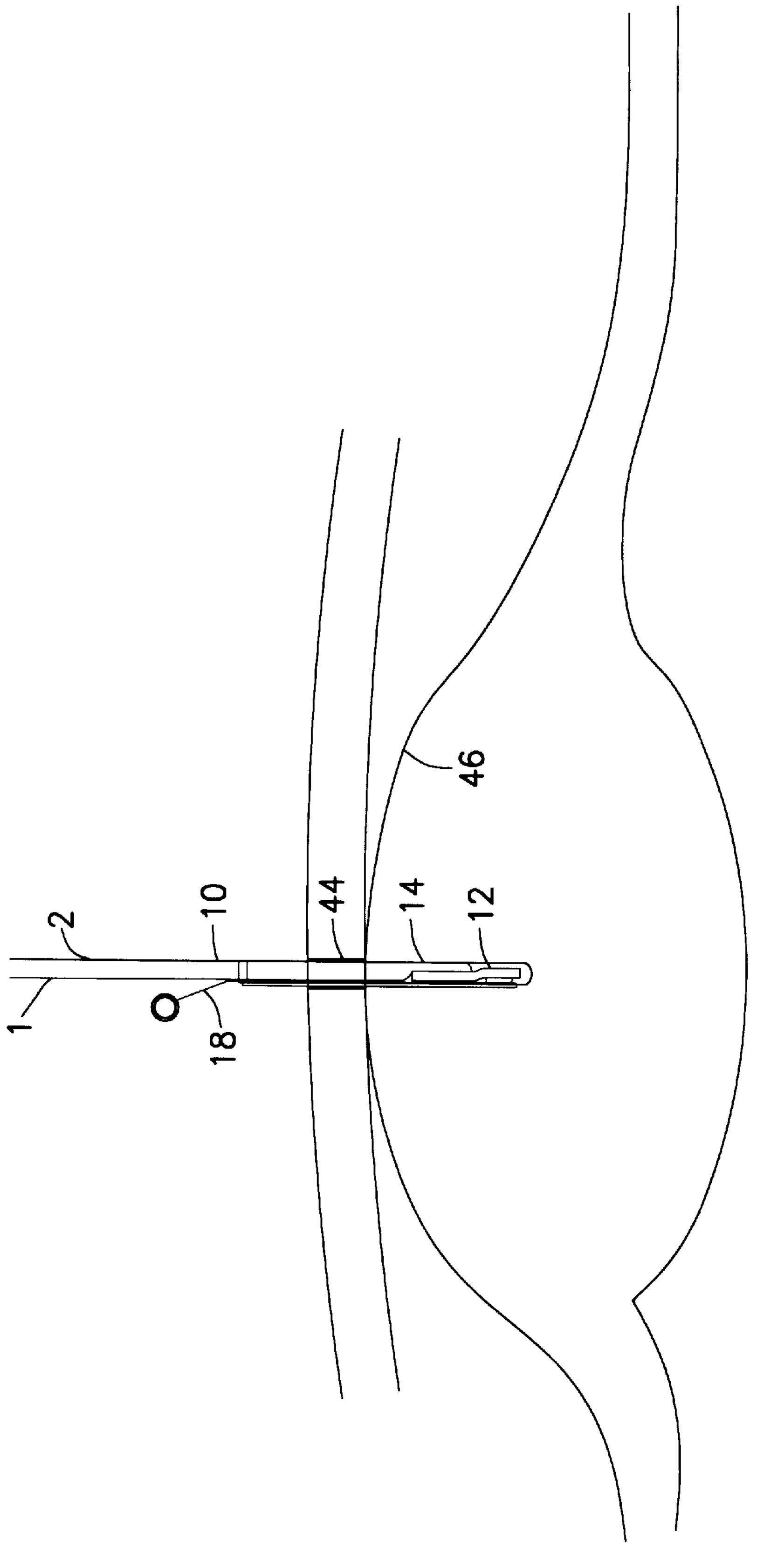
Figure 13:
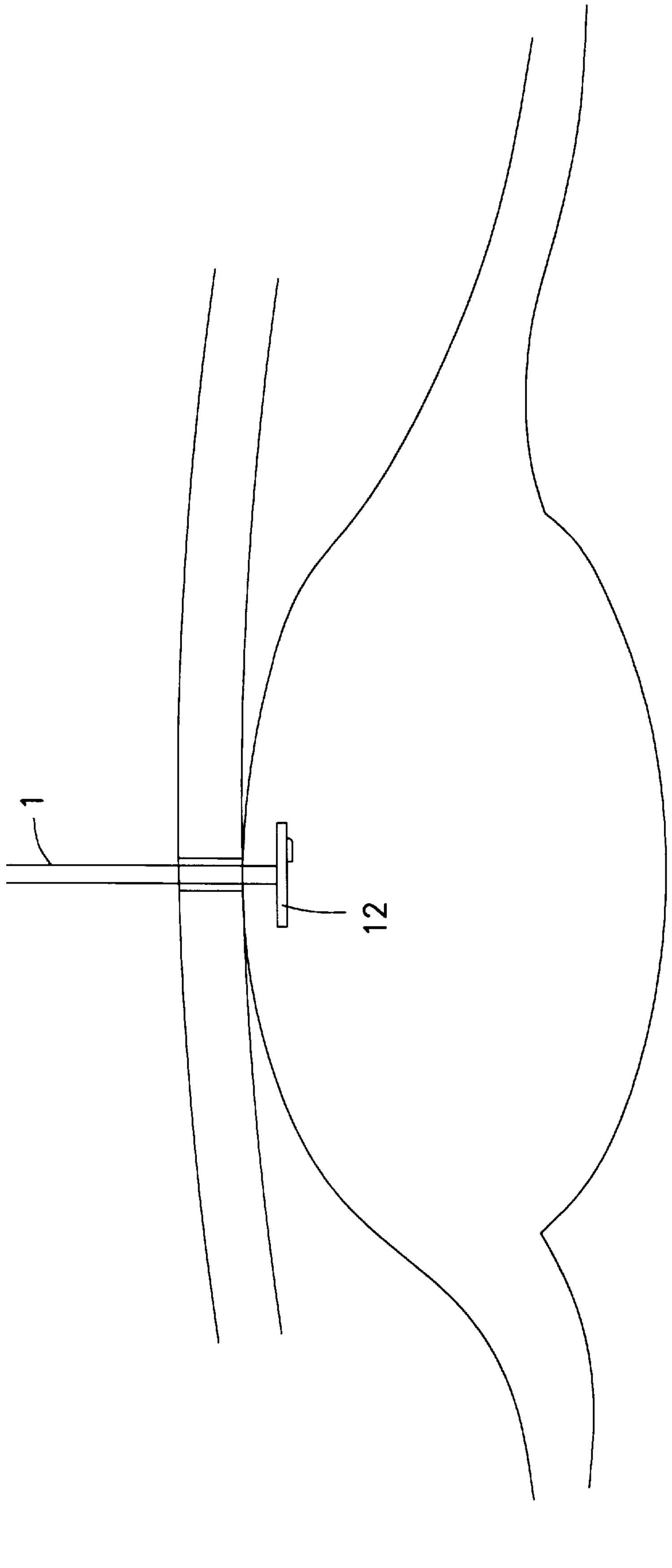

Next, the distal end of the gastrostomy assembly 2 is pushed through the stoma 44 until the internal bolster 12 is fully inserted into the stomach 46, as shown in FIG. 12. The practitioner performing the insertion can hold the tube 10 of the assembly 2 just proximally of the hollow sleeve, and push the assembly 2 through the stoma 44, with the lubricious outer surface of the sleeve 14 facilitating insertion. The rip cord 18 is then pulled, ripping the hollow sleeve 14 from the distal end towards the proximal end, thereby releasing the bolster 12 and allowing the bolster to regain its normal lateral extent upon release. The sleeve 14 and rip-cord 18 are then removed from the stoma 44, leaving the gastrostomy tube 1 in place, as shown on FIG. 13. The tube can then be adjusted, trimmed, and secured with an external bolster.

An alternate placement method of the present invention involves use of the embodiment shown in FIGS. 6*a* and 6*b*. In this embodiment the internal bolster 24 contains a pocket 26 capable of receiving an extension rod 21, as shown in FIGS. 6*a* and 6*b*. The method of inserting this embodiment includes essentially the same steps as those in method described above. In the alternate method, however, the apparatus is assembled such that the distal tip of the extension rod 21 can be placed within the pocket 26. The extension rod 21 is inserted into the pocket 26 and used to push the assembly through the stoma 44. The rod 21 is then removed from the stoma 44, and the rip cord 18 pulled to release the bolster 12, and the rip cord, sleeve and rod are removed.

Yet another placement method of the present invention, the embodiment described above, and shown in FIGS. 14*a* and 14*b*. In that embodiment, the gastrostomy assembly 2 includes a trocar 50 which facilitates placement directly through the body tissue where no prior penetration exists. The tapered distal end of the trocar 50 is used to pierce the body tissue and penetrate through to the target organ. The tapered distal end of the hollow sleeve 14 facilitates insertion of the assembly through the body tissue. Further facilitating insertion is the tapered wedge 54 of the trocar has a tapered edge 54 which engages the internal bolster 12 during insertion so that the sleeve 14 and bolster 12 are not pushed proximally with respect to the trocar 50 by the body tissue.

Figure 15:
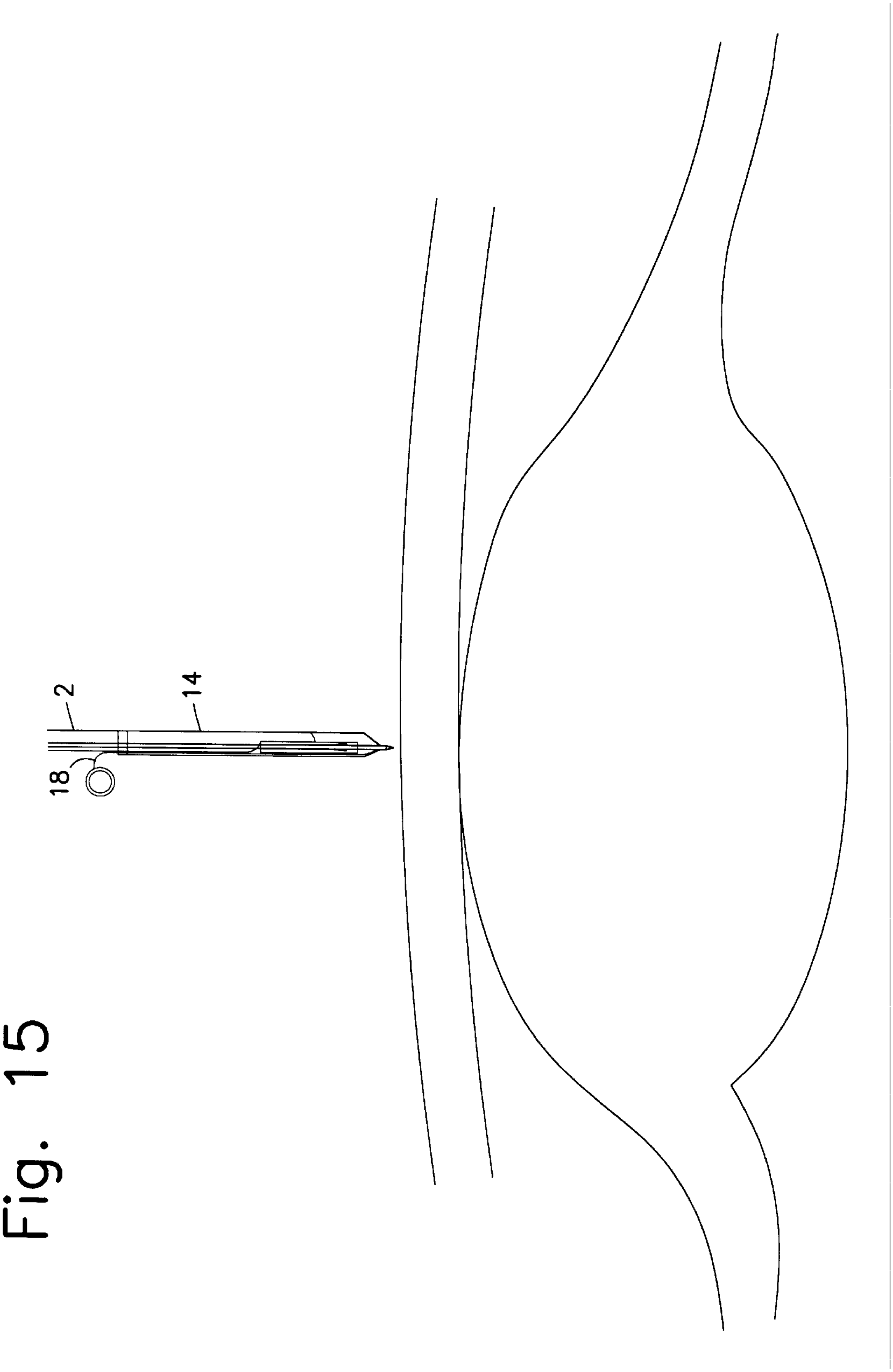
FIG. 15 shows a cross-sectional view of the abdominal wall and stomach, and an elevational view of the gastrostomy tube placement assembly having a trocar.

FIG. 15 shows the gastrostomy placement assembly 2 including trocar in relation to the abdominal wall. The trocar 50 is used to penetrate the tissue of the abdominal wall. Once the abdominal tissue has been pierced, the gastrostomy assembly 2 is pushed distally to penetrate the stomach wall. After the assembly 2 has sufficiently penetrated the stomach wall, the rip cord 18 is pulled which thereby releases the bolster 58 from the sleeve. The trocar 50, rip cord 18, and sleeve 14 are then removed from the penetration.

Still another placement method of the present invention involves the use of the embodiment which includes a cannula 56, as shown in FIG. 17. When placing a gastrostomy tube using a gastrostomy tube placement assembly 3 according to that embodiment, a penetration is formed which extends through the abdominal tissue and into the target organ, and a guidewire is placed within the penetration such that it extends external to the abdominal wall, using the Russell technique, for example. The gastrostomy assembly 3 is inserted over the guidewire such that the guidewire runs through the central lumen of the cannula 56. The assembly is pushed into the penetration and, once the gastrostomy assembly has sufficiently penetrated the target organ such that the internal bolster 12 is within the organ, the rip cord 18 is pulled, thereby tearing the sleeve 14, and releasing the bolster 12. The cannula 56, rip cord 18, and sleeve 14 are then removed.

What is claimed is:

1. A gastrostomy tube placement assembly comprising:

a gastrostomy tube having proximal and distal ends, and an internal bolster at its distal end which can be manipulated to have a reduced lateral extent; and an axially extending hollow sleeve having a proximal end, an inner surface and an outer surface, wherein said hollow sleeve can surround the internal bolster and hold the bolster in a position of reduced lateral extent; and a rip-cord which can be pulled, thereby ripping the sleeve and allowing the bolster to assume a position of increased lateral extent.

2. A gastrostomy tube placement assembly as set forth in claim 1, wherein the sleeve has a lubricous outer surface.

3. A gastrostomy tube placement assembly as set forth in claim 1, wherein the internal bolster can be folded such that it has reduced lateral extent.

4. A gastrostomy tube placement assembly as set forth in claim 1, wherein the internal bolster can be compressed such that it has reduced lateral extent.

5. A gastrostomy tube placement assembly as set forth in claim 1, wherein the internal bolster can be stretched such that it has reduced lateral extent.

6. A gastrostomy tube placement assembly as set forth in claim 1, wherein the internal bolster can pulled into the sleeve, thereby reducing the lateral extent of the bolster.

7. A gastrostomy tube placement assembly as set forth in claim 1, wherein the internal bolster can pushed into the sleeve, thereby reducing the lateral extent of the bolster.

8. A gastrostomy tube placement assembly as set forth in claim 1, wherein the sleeve can be reduced in diameter to fit around the internal bolster.

9. A gastrostomy tube placement assembly as set forth in claim 8, wherein the diameter of the sleeve can be reduced by shrinking the sleeve.

10. A gastrostomy tube placement assembly as set forth in claim 8, wherein the sleeve is capable of contracting such that the sleeve has a reduced diameter after contracting.

11. A gastrostomy tube placement assembly as set forth in claim 1, wherein the sleeve is made of a heat-shrinkable material.

12. A gastrostomy tube placement assembly as set forth in claim 1, wherein the sleeve is made of a fluoropolymer.

13. A gastrostomy tube placement assembly as set forth in claim 1, wherein the sleeve has a nick at the distal end.

14. A gastrostomy tube placement assembly as set forth in claim 13, wherein the rip-cord sits in the sleeve nick.

15. A gastrostomy tube placement assembly as set forth in claim 1, wherein the sleeve has two longitudinal slits 180° apart at the proximal end to aid in removal.

16. A gastrostomy tube placement assembly as set forth in claim 1, wherein the rip-cord runs distally between the hollow sleeve and internal bolster, wraps over the distal end of the sleeve and runs proximally along the longitudinal axis of the tube.

17. A gastrostomy tube placement assembly as set forth in claim 1, wherein the rip-cord is made of a filament.

18. A gastrostomy tube placement assembly as set forth in claim 1, wherein the rip-cord is integrally formed with the sleeve.

19. A gastrostomy tube placement assembly as set forth in claim 1, wherein the rip-cord has, at one end, a means for pulling the rip-cord.

20. A gastrostomy tube placement assembly as set forth in claim 1, wherein the gastrostomy tube has a handle at the proximal end.

21. A gastrostomy tube placement assembly comprising:

a gastrostomy tube having proximal and distal ends, and an internal bolster at its distal end which is manipulated such that it has a reduced lateral extent; and an axially extending hollow sleeve having a proximal end, an inner surface and an outer surface, wherein said hollow sleeve surrounds the internal bolster and holds the bolster in a position of reduced lateral extent; and a rip-cord which can be pulled, thereby ripping the sleeve so as to permit the bolster to assume a position of greater lateral extent.

* * * * *